April 27, 1976 N. BULL Plant Pat. 3,871
KALANCHOE PLANT
Filed Dec. 20, 1974
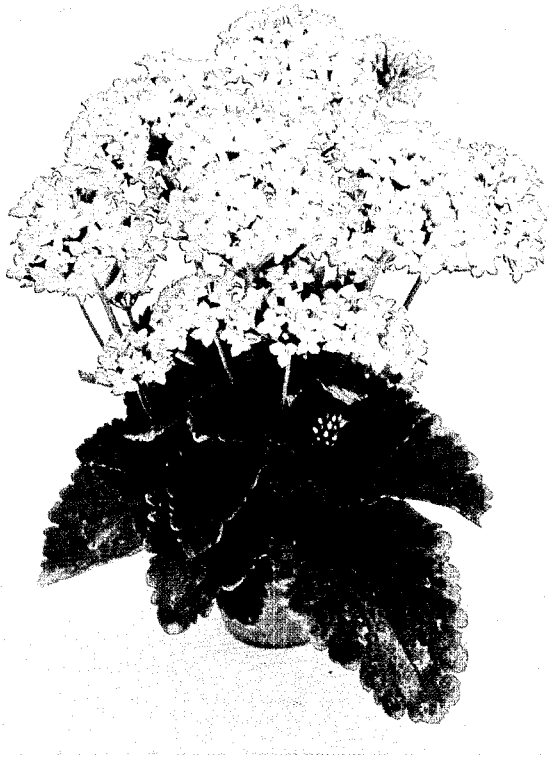

United States Patent

Plant Pat. 3,871
Patented Apr. 27, 1976

3,871
KALANCHOE PLANT

Norbert Buil, Gonnebek, Germany, assignor to Mikkelsens, Inc., Ashtabula, Ohio

Filed Dec. 20, 1974, Ser. No. 535,128
Int. Cl. A01h 5/00
U.S. Cl. Plt.—68 1 Claim The present invention relates to a new and distinct variety of Kalanchoe plant known by the varietal name Korall.

The new variety was discovered by me as a selected, cultivar seedling resulting from a cross between B101, the unnamed seed parent, and B103, the unnamed pollen parent. The new cultivar was asexually reproduced by stem cuttings at Gonnebek, West Germany, and the unique characteristics of the new cultivar have been transmitted through succesive propagations.

The new cultivar is particularly characterized by its beautiful and distinctive leaf structure, leaf size and shape of margins; very quick propagation, ease of flowering under adverse conditions during summer months; strong stems which carry large umbels; relatively large blooms, which have a diameter of 18 mm., coral red flower color, and by its durability and long keeping quality.

The natural blooming season of the new cultivar is mid to late January, although by steered culturing in the greenhouse, the cultivar can be brought to flowering during the entire year. Flowering response, as controlled by the initiation of the short day treatment, is 12 weeks in summer and 14–16 weeks in winter. The time from sticking of cuttings to flowering is 20 or 28 weeks for summer and winter, respectively.

The accompanying color photographic drawing shows a typical blooming plant of the new cultivar, with the color being as true as possible with color illustrations of this type.

The following is a detailed description of my new Kalanchoe variety based on plants produced under commercial practices grown in 12 cm. pots maturing mid July. Color references are made to the Royal Horticultural Society Colour Chart except where general terms of ordinary dictionary significance are used.

PARENTAGE

The new cultivator is a seedling resulting from crossing the seed parent B101, an unnamed and unpatented Kalanchoe variety, with the pollen parent B103, also an unnamed and unpatented Kalanchoe variety.

PROPAGATION

Asexually propagated true to type through the taking of stem cuttings.

(A) *Type cutting*: Stem cuttings, 15 mm. to 25 mm. long.
(B) *Time to root*:
10–12 days at 24° C., summer.
15–20 days at 20° C., winter.
(C) *Rooting habit*: Dentritic, profuse, fibrous.

PLANT DESCRIPTION (A) *Form*: Is erect, compact, close internodes, main stem measuring 10 mm. to 13 mm. in diameter.
(B) *Habit of growth*: Medium strong for kalanchoes of this type, some self branching but branches out well at a majority of the nodes when apical tip is removed during growth period.

(C) *Foliage description*: Foliage is abundant and noticeably attractive because of its clear green color, with crenated to double crenated edges.
(1) *Size*: Medium large for kalanchoes, measuring approximately 10 cm. wide by 11 to 12 cm. long. Leaf petiole 10 mm. to 12 mm. long.
(2) *Shape*: From oval to ovate, tip acute, base obtuse, pinnately veined.
(3) *Texture*: Upper—slightly rugose, thick, fleshy, coriaceous; under—glabrous.
(4) *Margin*: Heavily crenate to double crenate.
(5) *Color*: Young foliage, top side green 137–C, underside, green 138–B; mature foliage, top side green 137–B, underside, green 138–A.

FLOWERING DESCRIPTION (A) *Flowering habits*: Flowering is quite uniform in the total inflorescence; the number of flowering shoots (average six to eight, frequently 10) is dependent on the number of nodes initiating shoots after the removal of the apical tip; flowering shoots are self supporting in all but the darkest days of mid winter.
(B) *Natural flowering season*: In northern latitudes is mid January. Flowering time under controlled daylength at 22° C. in summer is 11–12 weeks; in winter is 12–13 weeks. Korall is not affected by heat delay in the summer as compared to the unpatented cultivar Mace or Roter Pfeffer, the latter being disclosed in my pending application Ser. No. 535,087, filed Dec. 20, 1974.
(C) *Flower bud description*: Upright, vase shaped, pointed at terminal before opening, petals rolled together and overlapping; color salmon red before opening. The bud is covered with four green sepals.
(D) *Flowers borne*: On compound paniculate cymes. The peduncle is approximately 14 to 17 cm. long; individual flower pedicels are approximately 3 to 6 mm. long.
(E) *Quantity of flowers*: Each peduncle carries an average of five cymes, each cyme developing approximately 30–35 flowers at one time. Additional flowers continue to develop.
(F) *Petals*:
(1) *Shape*: Oval, pointed at outward extremity.
(2) *Color*: Top side in summer, red 40A (Coral Red), when opening in summer, fading to red 41 A–B; underside, red 48 B–C.
(3) *Size*: Petals 5 mm. wide, 8 mm. long; flower, 17–18 mm. in diameter.
(4) *Number of petals*: Four, no overlapping, nearly horizontal and flat.
(G) *Reproductive organs*:
(1) *Stamens*: Number, generally eight.
(a) *Anther shape*: Typical, color brown.
(b) *Filament color*: Translucent, light green.
(c) *Pollen color*: Light yellow.
(2) *Pistils*:
(a) *Stigma*: Light green to crystalline white when receptive.
(b) *Style color*: Slender, cylindrical, light green.
(c) *Ovaries*: Number, four; size, 3–4 mm.; color, green.

DISEASE RESISTANCE

Highly resistent to botrytis and apparently immune to mildew when grown with older cultivars showing infectious of these diseases.

I claim:

1. A new and distinct cultivar of Kalanchoe plant particularly characterized by its beautiful and distinctive leaf structure, leaf size and shape of margins; very quick propagation, ease of flowering under adverse conditions during summer months; strong stems which carry large umbels; relatively large blooms, which have a diameter of 18 mm.; coral red flower color, and by its durability and long keeping quality.

No references cited.

ROBERT E. BAGWILL, Primary Examiner